US008301400B2

(12) United States Patent
Beard et al.

(10) Patent No.: US 8,301,400 B2
(45) Date of Patent: Oct. 30, 2012

(54) OPTIMAL SENSOR LOCATION FOR DAMAGE DETECTION

(75) Inventors: Shawn J. Beard, Livermore, CA (US); Xinlin Qing, Cupertino, CA (US); Tom Chang, Mountain View, CA (US); Lien Ouyang, Los Altos, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 818 days.

(21) Appl. No.: 12/061,494

(22) Filed: Apr. 2, 2008

(65) Prior Publication Data

US 2008/0255777 A1 Oct. 16, 2008

Related U.S. Application Data

(60) Provisional application No. 60/912,112, filed on Apr. 16, 2007.

(51) Int. Cl.
*G01B 5/28* (2006.01)
*G06F 19/00* (2006.01)

(52) U.S. Cl. ........................................... 702/35; 73/579

(58) Field of Classification Search .................... 702/33, 702/34, 35, 39, 181, 183; 73/579, 762; 324/209, 324/239; 600/407
See application file for complete search history.

(56) References Cited

U.S. PATENT DOCUMENTS 7,458,266 B2 * 12/2008 Beard et al. ..................... 73/579
2005/0284232 A1 * 12/2005 Rice ................................ 73/762
2006/0079747 A1 * 4/2006 Beard et al. .................. 600/407

* cited by examiner

*Primary Examiner* — John H Le
(74) *Attorney, Agent, or Firm* — Innovation Counsel LLP

(57) ABSTRACT

A method for determining optimal locations of a plurality of sensors for damage detection in a structural health monitoring system includes providing a one or more signal performance characteristics, spatial parameters describing a layout of a structure, and generating a layout for the plurality of sensors according to the signal performance characteristics and the spatial parameters. An estimated largest critical damage size that may not be detected by sensors arranged according to the first layout is determined. The layout is edited so as to reduce the estimated largest critical damage size to be less than or equal to a selected maximum size requirement.

22 Claims, 4 Drawing Sheets

OPTIMAL SENSOR LOCATION FOR DAMAGE DETECTION

CROSS-REFERENCE TO RELATED APPLICATION

This application claims the benefit of U.S. Provisional patent application Ser. No. 60/912,112, entitled "STRUCTURAL HEALTH MONITORING SYSTEM AND METHODS FOR USE," filed on Apr. 16, 2007, which is hereby incorporated by reference in its entirety.

BRIEF DESCRIPTION

This invention relates generally to structural health monitoring. More specifically, this invention relates to a methodology to determine the optimal placement of sensors to improve the reliability of damage detection.

BACKGROUND

In an ultrasound-based structural health monitoring system, the minimum detectable damage size is directly related to the geometry of the sensor network and the structure. A higher sensor density may enable detection of smaller sized damages. Placing sensors on a structure, where the sensors may be ultrasonic or acoustic wave transducers capable of both transmitting and receiving elastic wave signals, requires taking into account the shape of the structure, location and shape of stiffeners, ribs, cutouts and other forbidden zones where sensors may not or cannot be placed, propagation characteristics of the structural material, and characteristics of the sensors. Often, the sensor placement process may be ad hoc, and does not optimize the probability of detection of damage with the smallest possible critical damage size. Conventional approaches may result in an excessive number of sensors and consequent redundancy of information, higher signal processing demands, as well as greater material and computational cost. There is a need, therefore, for an automated method for designing the optimal placement of sensors on a structure to ensure reliable damage detection of the smallest possible sized damage.

SUMMARY

Methods are described for determining the optimal placement of sensors on a structure to ensure reliable damage detection.

In one embodiment, a method for determining optimal locations of a plurality of sensors for damage detection in a structural health monitoring system includes providing a one or more signal performance characteristics; providing spatial parameters describing a layout of a structure; generating a layout for the plurality of sensors according to the signal performance characteristics and the spatial parameters; determining an estimated largest critical damage size that may not be detected by sensors arranged according to the first layout; and editing the layout on the basis of the estimated largest critical damage size so as to reduce the estimated largest critical damage size until the largest estimated critical damage size is less than or equal to a selected maximum size requirement.

BRIEF DESCRIPTION OF THE FIGURES

Like element numbers in different figures represent the same or similar elements.

DETAILED DESCRIPTION

Figure 1:
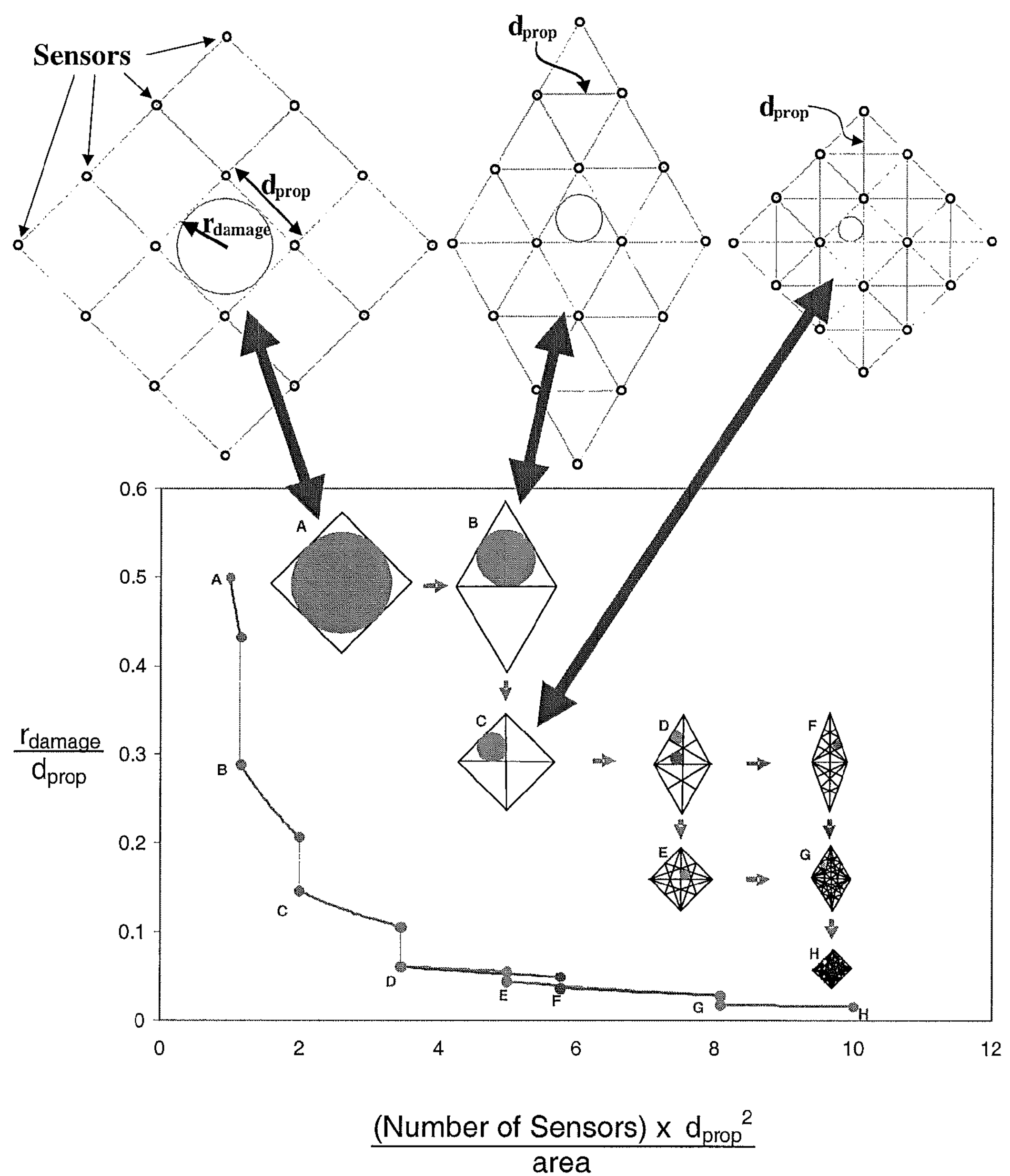
FIG. 1 illustrates a method of estimating detectable damage size in a structural health monitoring system according to an embodiment of the present disclosure.

In an ultrasound-based structural health monitoring system, the detectable damage size is directly related to the sensor network geometry. The higher the sensor density, the smaller the detectable damage size will be. There are at least two parameters that should be considered when sizing the sensor network: (1) the critical damage size that should be detected (e.g., having a radius larger than $r_{damage}$, a critical damage radius), and (2) the maximum distance a usable signal can propagate in the structure ($d_{prop}$). FIG. 1 illustrates how detectable damage size depends on sensor density and propagation distance, where $d_{prop}$ is selected as the maximum effective separation distance between sensors.

With knowledge of $r_{damage}$ and $d_{prop}$, an initial estimate of the sensor network configuration can be defined by using repeating unit cells, as shown in FIG. 1. For illustrative purposes, sensor layouts in FIG. 1 are depicted as square and equilateral triangle configurations of 16 sensors. $d_{prop}$ may be chosen as along an edge of a square or triangle, or along the diagonal of the square. Other configurations may be arranged within the scope of the disclosure. In one embodiment, the largest defect that may not be detected may be defined as the circle entirely contained within the square or triangle of paths formed by sensors spaced at the distance $d_{prop}$ or less. That is, the defect represented by the circle does not overlap any of the selected paths.

The several exemplary configurations shown in FIG. 1 illustrate how the minimum detectable damage size, represented by $r_{damage}$ normalized to the propagation distance $d_{prop}$, declines as the combined product of the number of sensors per unit area of the structure and the square of the propagation distance $d_{prop}$ increases. Since the propagation distance between sensors $d_{prop}$ may generally decrease as the number of sensors per unit area increases, it may be appreciated that increasing the density of the sensors may result in detecting smaller damage as $d_{prop}$ decreases. The area enclosed by a unit cell is proportional to $(d_{prop})^2$, thus the critical size detectable decreases accordingly.

In many cases, however, due to the complex geometry of the structure, it may not be possible to place sensors at the locations as prescribed by the estimate examples in FIG. 1. Therefore, an automated method beyond the estimation process illustrated in FIG. 1 is needed to determine the optimal locations of the sensors when a structure has stiffeners, cutouts, and other forbidden zones where sensors cannot be placed or where elastic waves cannot propagate, and to determine a probability of detection for damage of a critical size.

Figure 2:
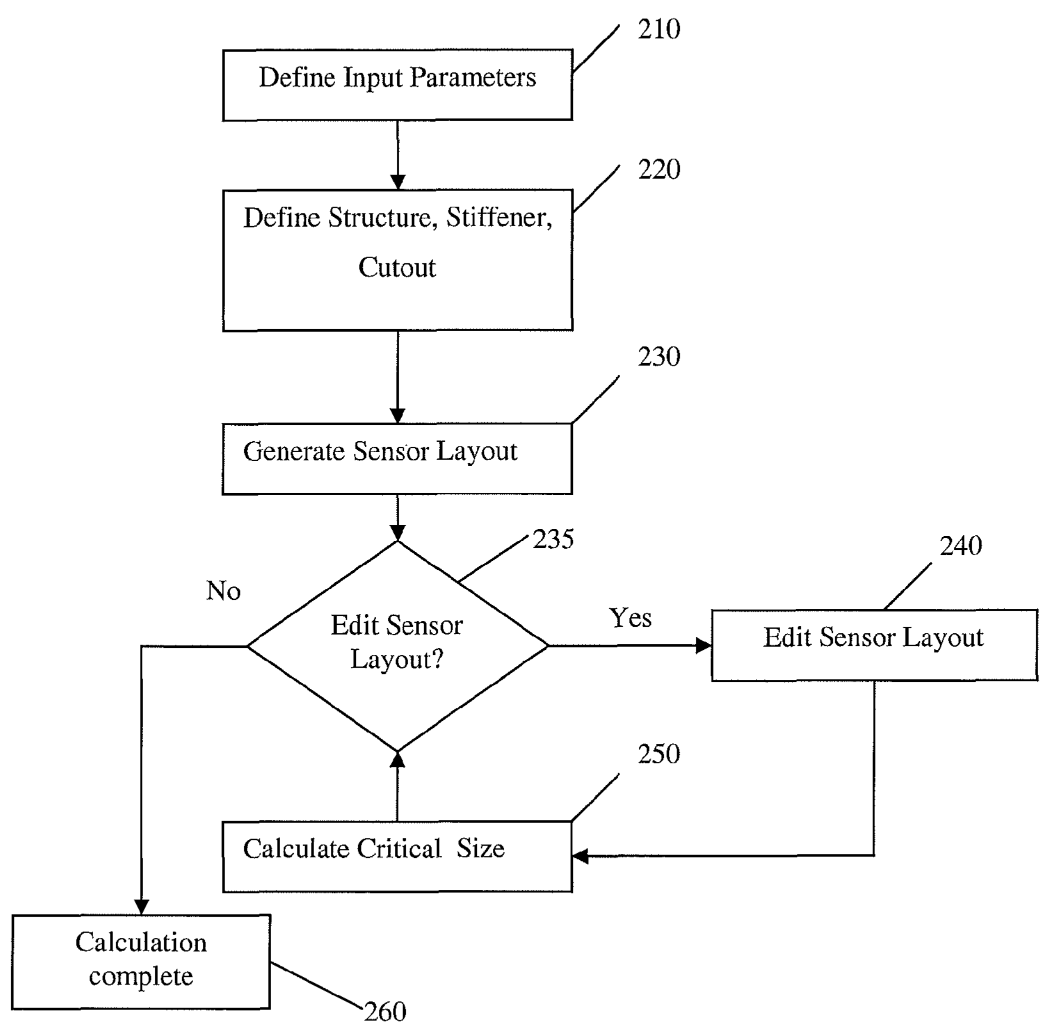
FIG. 2 is a flow diagram of a method to generate an optimal sensor layout according to an embodiment of the present disclosure.

FIG. 2 is a flow diagram of a method 200 to generate an optimal sensor layout to detect damage of a critical size. Input parameters relating to the signal performance characteristics, such as maximum propagation distance $d_{prop}$ and the largest size damage that may escape detection (characterized as a circle of critical damage radius $r_{damage}$), are input (block 210) to method 200. This step may be the estimation process described above. Any damage bigger than the critical size will be detected by overlapping with one or more sensor paths. Details of the structure may then be defined (block 220). Structure parameters detailed may include (but are not limited to) one or more of the geometry of the structure, which determines where sensors can be placed and what signal paths may be generated from this array of the sensors, the location of stiffeners, and whether sensors can be placed on or over stiffeners or ribs, whether signals can propagate through stiffeners or ribs, and the location of cutouts, where sensors cannot be placed, and signals may not propagate.

A layout of the sensor configuration is output (block 230) on the basis of the signal characteristics input in block 210 and the structure definition in block 220. The layout may include a list of sensors with location coordinates and the largest estimated critical damage size that may not be detected with the current layout. One may expect that the sensor configuration may comprise fewer sensors than the estimate corresponding to the unit cell model of FIG. 1. If a (manual or automated) decision is made to change the conditions of the design (a Yes decision in block 235) (such as, for example, requiring a change on the basis of the largest estimated critical damage size in the number/type of sensors, the size or shape of the structure, the placement or size of cutouts and/or stiffeners, or $d_{prop}$) the sensor and/or structure layout may be edited (block 240) the sensor layout is again calculated. The largest critical damage size that may exist and not be detected is calculated (block 250). If the result is not satisfactory, decision block 235 returns a Yes result and the layout editing procedure (block 240) may be repeated as needed. Following a No decision in block 235, the calculation is complete (block 260) and the critical damage size is provided.

Using method 200, the sensor layout may be rapidly prototyped for monitoring a structure and determining the minimum size damage the structural health monitoring system will detect, i.e., damage equal or greater than the calculated critical damage corresponding to a circle of radius $r_{damage}$. The designer may introduce variations in the structure and sensor layout by editing, if desired, and obtain a different result therefrom. The structure, stiffeners and cutouts may be modeled as polygons, and can be shaped, placed and removed as desired in structure definition (block (220) and/or editing (block 240). Sensors can be added, dropped, or have their specified locations and characteristics modified in edit block 240 as well.

Figure 3:
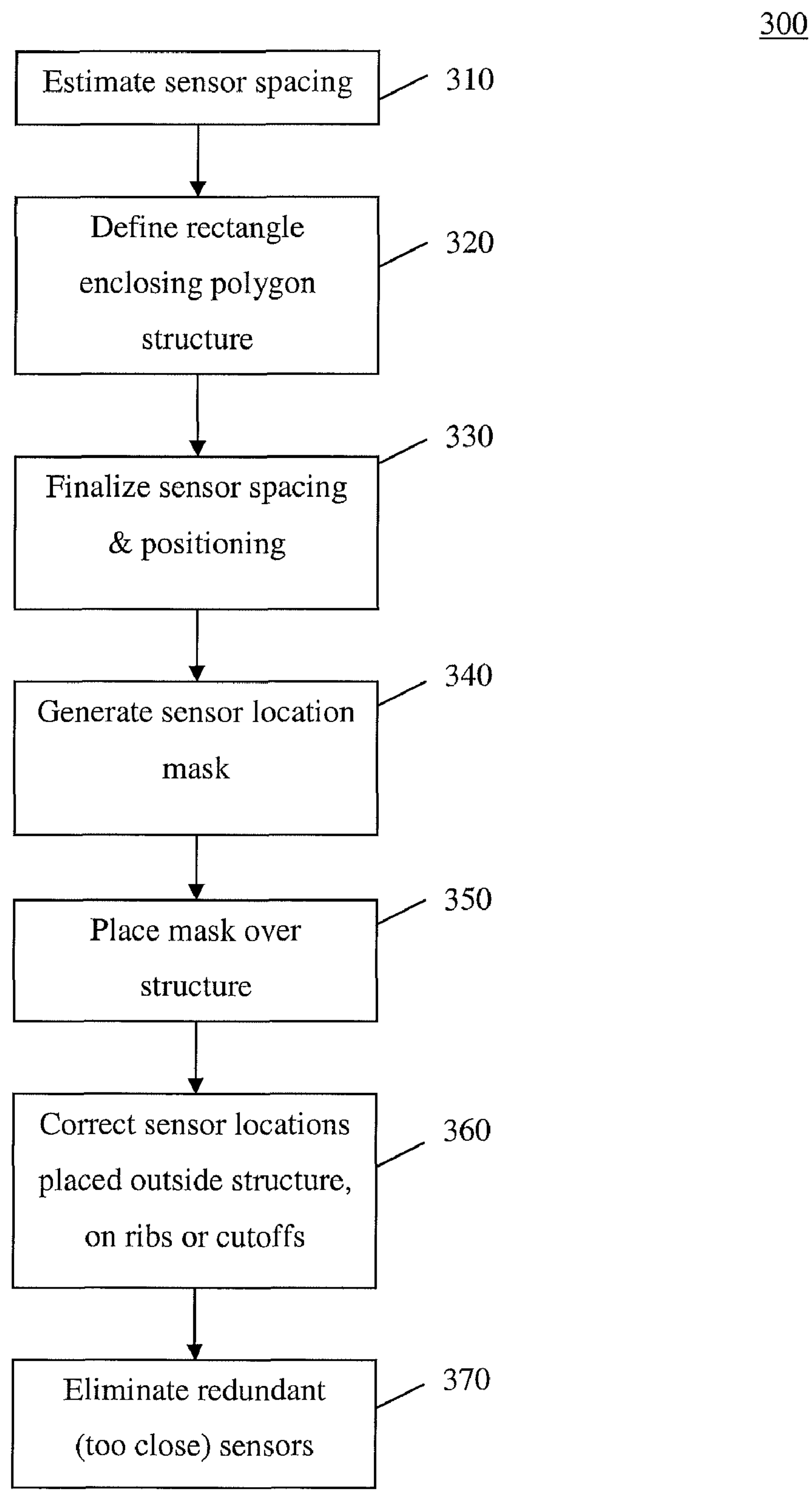
FIG. 3 is a flow chart of a method for specifying the location of sensors on a structure according to the present disclosure.

Sensor layout generation (blocks 230-240) may be described in more detail, as shown in FIG. 3, as a method 300 for specifying the location of sensors on a structure. Method 300 may include a first estimation of sensor spacing (block 310). This estimation may be based, for example, on the use of cell repetition as described in relation to FIG. 1, where a cell size, number of sensors, and propagation distance may be used to estimate the achievable critical damage size detectable.

The structure, or a portion thereof, may be regarded two dimensionally as a quasi-planar surface (for the simplifying purpose of specifying the location of sensors using coordinates in only two dimensions, it being understood that the sensors are placed on the surface of the structure, and the surface may have curvature in one or two dimensions). A rectangle may be defined that encloses the polygon outline of the structure (block 320). This defines Xmin, Xmax, Ymin, and Ymax dimensional limits of the polygon. The rectangular area so defined may be used as a first topography for populating the structure with sensors.

Within the edge of the rectangle defined in block 320, a border of specified dimension may be established (block 330), thus avoiding placement of sensors any closer to the rectangle minimum or maximum coordinates than the specified border dimension. Additionally, in block 330, using the sensor spacing estimation method of block 310 as a starting point, the number of cells, and therefore the number of sensors may be estimated. This estimate can be rounded (up or down) to an integer value. Rounding up will increase the detectability of damage of a smaller critical size. Sensor positioning is then first estimated in block 330 according to the cell layout used. The spacings between sensors that result are dX and dY. The number and placement of sensors may change due to subsequent steps of the method 300.

A mask (i.e., an overlay map) of the sensor locations may be generated (block 340). The mask includes the matrix of coordinates of the sensors. The mask (i.e., matrix) may be superimposed on the structure (block 350). The structure, which is represented as a polygon, may not be identical to the rectangle. Therefore, some sensor locations may fall outside the structure polygon. Block 360 then proceeds to shift the outside sensors in the +/−X and/or +/−Y directions, inside the border generated in block 330 by an amount not to exceed a value dX or dY, since shifting a sensor by these amounts will position a sensor over the same location as an adjacent sensor, which may introduce redundancy, discussed below.

Block 350 has placed all sensors on the structure, and inwardly from the edge by the border dimension. Block 360 may then correct for sensors located over cutouts, and moves them away from such forbidden locations in +/−X and/or +/−Y as far as is needed. Because there is no preference specified as to direction of motion, all four displacements may be generated. Thus, up to four new sensor locations may be created in the elimination of the one located in a cutout area.

After the sensor location adjustments of blocks 235 and 360 have been performed, some sensors may be clustered adjacent to one or more other sensors by less than a specified minimum spacing distance, thus, introducing redundancy. Sensors found to be spaced less than the specified minimum spacing distance apart are deemed redundant and one of the sensors may be eliminated (block 370). The choice of elimination may be made on the basis of various criteria. For example, the sensor moved the greater distance may be the one selected for elimination. Alternatively, a sensor may be selected for elimination if the remaining choice(s) may later allow for detection of a damage of smaller critical size.

Figure 4:
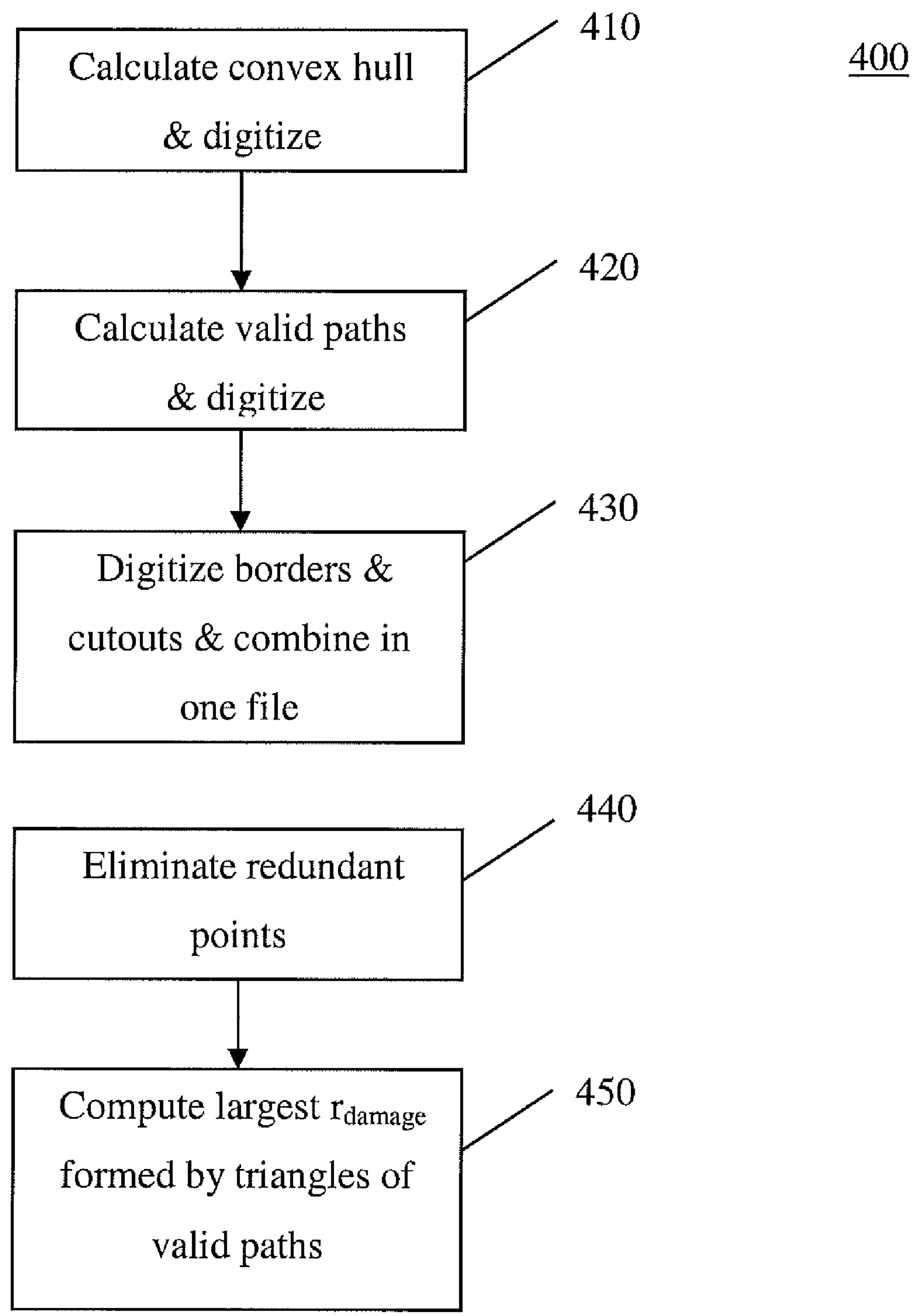
FIG. 4 is a flow chart of a method of calculating the detectable critical size of damage in a structure according to an embodiment of the disclosure.

FIG. 4 is a flow chart of a method 400 of calculating the detectable critical size of damage in a structure according to an embodiment of the disclosure. Method 400 includes calculating the convex hull (block 410) of sensor locations and discretizing, or digitizing, the locations. A convex hull, or convex envelope for a set of points, is the minimal convex set containing the points X. In this case, the convex hull is the minimum size convex polygon that encompasses all the sensor locations as arranged on the structure using method 300. Therefore, it may be visualized as a polygon connecting the outermost sensors on the structure, having the minimum size perimeter. Numerous algorithms for computing a convex hull are well known in computational geometry.

Within the convex hull, all valid paths between sensors that are shorter than the given maximum signal traveling distance $d_{prop}$ may be calculated (block 420) and the paths may be digitized in selected increments of distance along each of the paths. The digitized paths, borders and cutouts may be digitized in the same manner as for sensor paths and combined in a single file (block 430) with the digitized paths for further calculations. Based on the locations of the sensors, borders and paths, redundant points may be eliminated (block 440). That is, for example, where the convex hull border has overlapping valid sensor paths, and therefore does not require duplication, only one digitized path may be required. Not all digitized portions of the convex hull are valid sensor paths (where, for example, the length exceeds the maximum propagation distance).

Given the resulting set of valid paths (i.e., where the path length is equal or less than the maximum propagation distance $d_{prop}$) and sensor locations, where the valid paths have been digitized in selected increments of distance, the largest damage, as defined by $r_{damage}$, may be calculated (block 450) as follows: Triangular regions may be defined by the selected paths formed by three sensors. The largest inscribed circle that may be enclosed in the triangle formed by three such paths without touching any path is the critical size damage of radius $r_{damage}$. Any damage of radius larger than $r_{damage}$ centered within the triangular region will be detected by intersection with one or more of the selected paths formed by the three transducers.

However, a fast estimation procedure may be used to obtain an approximation of the critical damage size, so that sensor layout editing may be accomplished more quickly, as follows: The sensor paths may be digitized with a few selected coordinate points spaced, for example, at selected intervals along the paths. These points form a set nominally in two dimensions. A set of triangles may be formed from any arbitrary combination of three points in the set thus created. The radius of the circle circumscribing each triangle thus formed is a candidate for $r_{damage}$, the radius of the largest size damage that may escape detection. The radius of the largest circumscribed circle found out of all such circles formed is selected as an approximation of the critical damage radius $r_{damage}$.

Establishing all triangles automatically from which the largest critical damage size may be obtained (block 450) may be performed in numerous ways. For example, various versions of the Delaunay triangulation algorithm may be applied to automatically find all such triangles. In the Delaunay method, each triangle that is formed from a triplet of selected digitized points, where each point comes from a different valid path, will have a circumscribed circle surrounding the triangle on the condition that the circle does not include a fourth digitized point inside that circle, i.e., the Delaunay method excludes other digitized points from the circumscribed circle.

If the center of the circumscribed circle formed in each case happens to fall outside the convex hull, that circle may be ignored, and a damage radius is not computed. Otherwise, the largest radius circle may be determined from comparing all the circumscribed circles formed from the digitized points inside the convex hull (block 450). The result is a fast approximation of the critical damage size such that any damage larger than this will be detected as it must intersect a valid path. The Delauney triangulation method may be applied with a finer grid of point digitization on each sensor path. This will result in a more accurate value of critical damage size. However, the benefit derived from greater computational speed using a coarse digitization grid may be substantial, with little sacrifice to accuracy. For example, choosing a digitization grid that results in an estimated critical damage size within 10% of the exact value may be sufficient, as determined by a user. Other methods of determining the largest critical size radius may be applied within the scope and meaning of the present disclosure.

If method 200 results in placing transducers in an irregular pattern, the critical damage size may vary in different regions of the structure due to the differences in the triangles formed. In this case, the largest circle found for the entire structure may be designated as the critical damage size.

Although the present disclosure has been described with reference to certain exemplary embodiments thereof, it will be understood by those skilled in the art that a variety of modifications and variations may be made without departing from the spirit or scope of the present disclosure defined in the appended claims, and their equivalents.

What is claimed is:

1. A method for determining optimal locations of a plurality of sensors for damage detection in a structural health monitoring system, comprising:
- providing one or more signal performance characteristics of the plurality of sensors;
- providing spatial parameters describing a layout of a structure;
- generating a layout for the plurality of sensors on the structure according to an estimated spacing between the plurality of sensors, the estimated spacing based on the signal performance characteristics and the spatial parameters;
- determining an estimated largest critical damage size on the structure that may not be detected by sensors arranged according to the first layout; and
- editing the layout on the basis of the estimated largest critical damage size so as to reduce the estimated largest critical damage size to be less than or equal to a selected maximum size requirement.

2. The method of claim 1, wherein the signal performance characteristics further comprise:
- a maximum propagation distance of structural health monitoring signals between any pair of the sensors; and
- a largest size damage that can escape detection; wherein the largest size damage that can escape detection is characterized by a circle of a radius $r_{damage}$.

3. The method of claim 1, wherein the providing further comprises:
- specifying a geometry for the structure; and at least one of:
- indicating locations of one or more ribs and/or stiffeners, and
- identifying locations of one or more regions cut out from the structure.

4. The method of claim 1, further comprising defining a rectangular area enclosing a polygon area, wherein the polygon area is an outline of the structure.

5. The method of claim 4, wherein the editing further comprises:
- specifying a border within the rectangular area;
- superimposing the layout on the rectangular area; and
- correcting the locations of sensors by one or more correcting distances that do not exceed the estimated spacing between the plurality of sensors.

6. The method of claim 5, wherein the correcting further comprises:
- adjusting the locations of sensors placed outside the polygon area to locations inside the polygon area; and
- adjusting the locations of sensors placed within one or more of the cut out regions to locations outside the one or more of the cut out regions.

7. The method of claim 6, wherein the correcting further comprises:
- adjusting the locations of sensors placed within the one or more ribs or stiffeners to locations outside the one or more ribs or stiffeners.

8. The method of claim 7, wherein the correcting further comprises eliminating one or more sensors in corrected locations when one of the sensors is spaced at a distance less than a selected minimum spacing from another of the sensors.

9. The method of claim 8, wherein the calculating the estimated largest critical size damage that may escape being detected comprises:

determining a convex hull for the sensor layout;

identifying all valid paths between pairs of the sensors, the valid paths having sensors spaced a distance equal or less than a maximum propagation distance;

digitizing the convex hull, the valid paths, and the borders of the cutouts according to specified increments of spacing;

eliminating redundant points corresponding to digitized points that are spaced apart a distance less than the specified increment of spacing; and determining radii of circles circumscribing each triangle formed by selecting a first set of three digitized points along two or more of the valid paths;

repeating the determining for all triangles that may be formed by selecting differing sets of three digitized points from two or more of the valid paths until all triangles have been specified and the corresponding circumscribing circle radius has been computed for each triangle;

repeating the computing for all sets of valid paths; and selecting the radius of the largest of the circumscribing circles as the largest estimated critical size damage radius that may escape detection.

10. The method of claim 9, wherein the computing the triangles is performed according to a Delaunay triangulation method.

11. The method of claim 10, wherein a computed circumscribing circle having a center located outside the convex hull is ignored, and no corresponding damage radius is computed.

12. A non-transitory computer-readable medium containing computer instructions stored therein for carrying out a method for determining optimal locations of a plurality of sensors for damage detection in a structural health monitoring system, the method comprising:

providing one or more signal performance characteristics;

providing spatial parameters describing a layout of a structure;

generating a layout for the plurality of sensors according to an estimated spacing between the plurality of sensors, the estimated spacing based on the signal performance characteristics and the spatial parameters;

determining an estimated largest critical damage size that may not be detected by sensors arranged according to the first layout; and editing the layout on the basis of the estimated largest critical damage size so as to reduce the estimated largest critical damage size to be less than or equal to a selected maximum size requirement.

13. The non-transitory computer-readable medium of claim 12, wherein the signal performance characteristics further comprise:

a maximum propagation distance of structural health monitoring signals between any pair of the sensors; and a largest size damage that can escape detection; wherein the largest size damage that can escape detection is characterized by a circle of a radius $r_{damage}$.

14. The non-transitory computer-readable medium of claim 12, wherein the providing further comprises:

specifying a geometry for the structure; and at least one of:

indicating locations of one or more ribs or stiffeners, and identifying locations of one or more regions cut out from the structure.

15. The non-transitory computer-readable medium of claim 12, further comprising defining a rectangular area enclosing a polygon area, wherein the polygon area is an outline of the structure.

16. The non-transitory computer-readable medium of claim 15, wherein the editing further comprises:

specifying a border within the rectangular area;

superimposing the layout on the rectangular area; and correcting the locations of sensors by one or more correcting distances that do not exceed the estimated spacing between the plurality of sensors.

17. The non-transitory computer-readable medium of claim 16, wherein the correcting further comprises:

adjusting the locations of sensors placed outside the polygon area to locations inside the polygon area; and adjusting the locations of sensors placed within one or more of the cut out regions to locations outside the one or more of the cut out regions.

18. The non-transitory computer-readable medium of claim 17, wherein the correcting further comprises:

adjusting the locations of sensors placed within the one or more ribs or stiffeners to locations outside the one or more ribs or stiffeners.

19. The non-transitory computer-readable medium of claim 18, wherein the correcting further comprises eliminating one or more sensors in corrected locations when one of the sensors is spaced at a distance less than a selected minimum spacing from another of the sensors.

20. The non-transitory computer-readable medium of claim 19, wherein the calculating the estimated largest critical size damage that may escape being detected comprises:

determining a convex hull for the sensor layout;

identifying all valid paths between pairs of the sensors, the valid paths having sensors spaced a distance equal or less than a maximum propagation distance;

digitizing the convex hull, the valid paths, and the borders of the cutouts according to specified increments of spacing;

eliminating redundant points corresponding to digitized points that are spaced apart a distance less than the specified increment of spacing; and determining radii of circles circumscribing each triangle formed by selecting a first set of three digitized points along two or more of the valid paths;

repeating the determining for all triangles that may be formed by selecting differing sets of three digitized points from two or more of the valid paths until all triangles have been specified and the corresponding circumscribing circle radius has been computed for each triangle;

repeating the computing for all sets of valid paths; and selecting the radius of the largest of the circumscribing circles as the largest estimated critical size damage radius that may escape detection.

21. The non-transitory computer-readable medium of claim 20, wherein the computing the triangles is performed according to a Delaunay triangulation method.

22. The non-transitory computer-readable medium of claim 21, wherein a computed circumscribing circle having a center located outside the convex hull is ignored, and no corresponding damage radius is computed.

* * * * *